United States Patent [19]

Moroni

[11] Patent Number: 4,528,393

[45] Date of Patent: Jul. 9, 1985

[54] DERIVATIVES HAVING EXPECTORANT ACTIVITY, THE PROCEDURE FOR THEIR PREPARATION AND THE PHARMACEUTICAL COMPOSITIONS WHICH CONTAIN THEM

[75] Inventor: Adolfo Moroni, Brescia, Italy

[73] Assignee: Magis Farmaceutici S.R.L., Brescia, Italy

[21] Appl. No.: 536,737

[22] Filed: Sep. 28, 1983

[51] Int. Cl.³ ............................................. C07C 69/76
[52] U.S. Cl. ..................................... 514/539; 560/61
[58] Field of Search ........................... 560/61; 424/308

[56] References Cited

PUBLICATIONS

Curti, P. C., Pneumonologie, 147(1), 62–74, 1972.
Seydel, J. K. et al., Biochem. Pharmacol., 25(21), 2357–64, 1976.
Eckert, H. et al., Lung, 161(4), 213–18, 1983.
Wauer, R., Symp. Giovanni Lorenzini Found., 16(Pulm. Surfactant Syst.), 173–88, 1983.

*Primary Examiner*—Paul J. Killos
*Attorney, Agent, or Firm*—Stevens, Davis, Miller & Mosher

[57] ABSTRACT

New esters of N-(2-amino-3,5-dibromobenzyl)trans-4-aminocyclohexanol, along with certain phenolic derivatives, present interesting expectorant activity, associated with an acute toxicity which is very low. They are, therefore, useful as active principles in pharmaceutical compositions, for oral, topical, injection and rectal use, and are especially indicated for the treatment of bronchial affections.

21 Claims, No Drawings

DERIVATIVES HAVING EXPECTORANT ACTIVITY, THE PROCEDURE FOR THEIR PREPARATION AND THE PHARMACEUTICAL COMPOSITIONS WHICH CONTAIN THEM

The new derivatives of N-(2-amino-3,5-dibromobenzyl)-trans-4-amino-cyclohexanol, which will hereafter be called ambroxol for brevity, form the object of this invention, together with the procedure for their preparation and the pharmaceutical compositions that contain them. The new compounds forming the object of this invention, have the following formula (I):

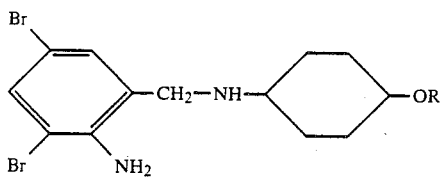

where R represents the groups guaiacolglycolyl, (4-methylguaiacol)glycolyl, m-cresolglycolyl, o-cresolglycolyl, p-cresolglycolyl, thymoglycolyl, carvacrolglycolyl or guaiacolcarbonyl. Object of the invention are also the pharmaceutically acceptable salts of the same compounds.

These salts which are pharmaceutically acceptable include the nontoxic salts obtained by the addition of acids, either organic or inorganic, such as for example hydrochloric acid, hydrobromic acid, hydroiodic acid, phosphoric acid, sulphuric acid, maleic acid, citric acid, acetic acid, oxalic acid, succinic acid, benzoic acid, tartaric acid, fumaric acid, mandelic acid, ascorbic acid and malic acid.

The following table gives the corresponding formula structure and assigned code number, for simplicity, for each formula (I) compound for the relative group represented by R.

SUMMARY TABLE

| Formula Structure: OR | Group Represented by R | Formula (I) Compound Code No. |
|---|---|---|
| OCH₃ / OCH₂COO— (benzene) | guaiacolglycolyl | E/6001 |
| O—CH₂—COO— / OCH₃ / CH₃ (benzene) | (4-methylguaiacol)glycolyl | E/6002 |
| O—CH₂—COO— / CH₃ (benzene) | m-cresolglycolyl | E/6003 |
| O—CH₂—COO— / CH₃ (benzene) | o-cresolglycolyl | E/6004 |
| O—CH₂—COO— / CH₃ (benzene) | p-cresolglycolyl | E/6005 |
| CH₃ / O—CH₂—COO— / CH(CH₃)₂ | thymoglycolyl | E/6006 |
| CH₃ / O—CH₂—COO— / CH(CH₃)₂ | carvacrolglycolyl | E/6007 |
| OCH₃ / OCOO (benzene) | guaiacolcarbonyl | E/6008 |

The new formula (I) compounds and their pharmaceutically acceptable salts have a therapeutically useful expectorant activity. Further object of this invention, therefore, are the pharmaceutical compositions characterized by the fact that they contain an effective quantity of one or more of the formula (I) compounds and/or their pharmaceutically acceptable salts as active principles, just as they are or in combination with vehicles, diluents, solvents and/or pharmaceutically acceptable excipients.

A further object of this invention is the process for the preparation of the formula (I) compounds and their pharmaceutically acceptable salts, characterized by the fact that the trans-1-bromo-4-aminocyclohexane, having the following formula (II):

is made to react with the formula (III) compound, i.e. 2-amino-3,5-dibromo-benzaldehyde,

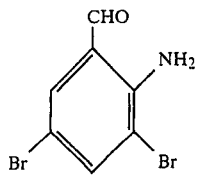

to obtain the aldiminic intermediate of formula (IV):

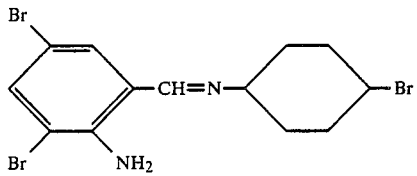

which is reduced with hydrogen in the presence of Nickel-Raney to obtain N-(2-amino-3,5-dibromobenzyl)-trans-4-amino-1-bromo-cyclohexane having formula (V),

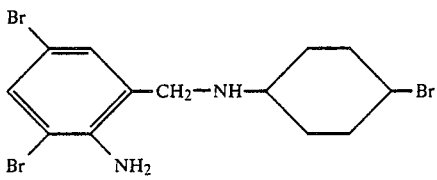

which is made to react with an acid of formula:

ROH  (VI)

where R is as defined above, in the presence of an alkaline carbonate and of a catalyst, to obtain the corresponding formula (I) compound, as defined above, which, optionally, is salified. The new formula (I) compounds and their pharmaceutically acceptable salts, which form the object of this invention, have expectorant characteristics which are very useful for therapeutic applications. Very surprisingly, their expectorant activity is 1.1 to 1.6 times greater than ambroxol hydrochloride. Also very surprisingly, the new formula (I) compounds, as compared to ambroxol, have much better gastric tolerability and are absorbed more rapidly, reaching the maximum hematic levels 3 to 4 times more rapidly than the ambroxol. The peak level in the blood is reached 20–40 minutes after oral administration. This determines higher concentrations of active principle. With dogs, the half-life of the new derivatives in the blood is from 25–30 hours. It is also to be underlined that the new compounds are stable in both the stomach and the intestinal tract, hydrolizing after being absorbed. The complete reliability of the new compounds was determined by evaluating their acute toxicity. Acute toxicity was studies in the mouse, rat and guinea pig, comparing with ambroxol hydrochloride. The $DL_{50}$ values were calculated by following the Litchfield and Wilcoxon method (Pharm. Exp. Therap. 1949, 96,99). The obtained results are shown in Table 1 and indicate that the new compounds are reliable, with $DL_{50}$ values substantially comparable or better than those of ambroxol.

TABLE 1

| Compound Administered | Type of Animal | Acute Toxicity $DL_{50}$. mg/kg (95% fid. lim.) | | |
|---|---|---|---|---|
| | | i.v. | i.p. | os |
| Ambroxol Hydrochlorate | mouse | 138 | 268 | 2750 |
| | rat | — | 380 | 13400 |
| | guinea pig | — | 280 | 1180 |
| E/6001 | mouse | 194 | 375 | 3850 |
| | rat | — | 532 | 18700 |
| | guinea pig | — | 390 | 1650 |
| E/6002 | mouse | 201 | 390 | 4000 |
| | rat | — | 550 | 19560 |
| | guinea pig | — | 400 | 1700 |
| E/6003 | mouse | 187 | 360 | 3700 |
| | rat | — | 510 | 18000 |
| | guinea pig | — | 380 | 1600 |
| E/6004 | mouse | 187 | 365 | 3700 |
| | rat | — | 500 | 18000 |
| | guinea pig | — | 375 | 1610 |
| E/6005 | mouse | 180 | 360 | 3700 |
| | rat | — | 500 | 17800 |
| | guinea pig | — | 380 | 1600 |
| E/6006 | mouse | 197 | 380 | 3900 |
| | rat | — | 540 | 19000 |
| | guinea pig | — | 400 | 1680 |
| E/6007 | mouse | 190 | 390 | 3900 |
| | rat | — | 530 | 18500 |
| | guinea pig | — | 410 | 1700 |

Therefore, thanks to the above-described properties, the new compounds—which constitute the object of this invention—are particularly useful as active principles for pharmaceutically compositions, either just as they are or combined with vehi les, diluents, solvents and/or pharmaceutically acceptable excipients. The said pharmaceutical compositions can be in solid form as, for example, a capsule, pill or the like, or they can be in liquid form as, for example, ready-to-use or extemporaneous solutions or emulsions, spray solutions or ready-to-use or extemporaneous solutions for intramuscular (im) or endovenous (ev) injection. In the treatment of bronchial affections, the new compounds which form the object of this invention can be administered orally, by injection, by spraying or rectally. Oral administration, for example, can consist of from 45 to 135 mg of active principle as a posological unit, administered 2, 3 or 4 times per day. The posological unit for im or ev injection can, for example, be from 15 to 45 mg of active principle, administered 2, 3 or 4 times per day. The posological unit for spray treatment can, for example, be from 15 to 30 mg of active principle, administered 2, 3 or 4 times per day. The posological unit for rectal administration can, for example, be from 15 to 90 mg of active principle, administered 2, 3 or 4 times per day. All the above-mentioned pharmaceutical compositions can be prepared in accordance with methods which are well known to the technician in this field, using vehicles, solvents, diluents and/or well-known excipients. The text, "Tecnologia Farmaceutica" by S. Casadia-Ed.Cisalpino Goliardica, Milano, 1972 covers the subject very completely.

The compounds which form the object of this invention can be prepared—and this process is also part of the object of this invention—by reacting N-(2-amino-3,5-dibromobenzyl)-trans-4-amino-1-bromo-cyclohexane (V), which is obtained by reducing the aldimine, (IV), with an ROH (VI) acid, where R is as defined above, in the presence of an alkaline carbonate and a catalyst; and, optionally, salifying the obtained formula (I) compound. The reaction is usefully carried out in an organic solvent, advantageously with N,N-dimethylformamide.

The alkaline carbonate is preferably sodium carbonate or potassium carbonate and the catalyst is either sodium or potassium iodide. The optional salification is conducted using well-known methodologies as, for example, by adding the appropriate acid to a formula (I) compound solution. The aldimine (IV) is obtained by reacting the trans-4-amino-1-bromocyclohexane (II) with the 2-amino-3,5-dibromobenzaldehyde. Trans-4-amino-1-bromocyclohexane (II) is obtained in the form of a hydrochloride—which also forms part of the object of this invention—by a process which is characterized by the fact that trans-4-amino-cyclohexanol (VII),

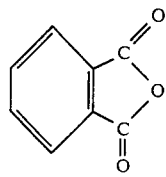
(VII)

is made to react with phthalic anhydride (IX),

(IX)

to obtain the corresponding phthalimide (VIII),

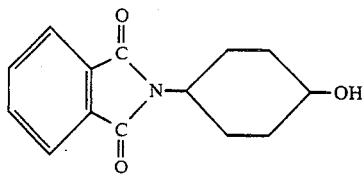
(VIII)

which is brominated with phosphorus tribromide (X) to obtain the bromo derivative (XI),

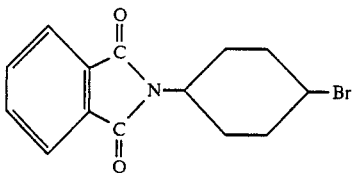
(XI)

which, by hydrolysis with concentrated hydrochloric acid, gives compound (II) in the form of hydrochloride. The process for the preparation of the formula (I) compounds, starting off with trans-4-amino-cyclohexanol, is schematically shown as follows:

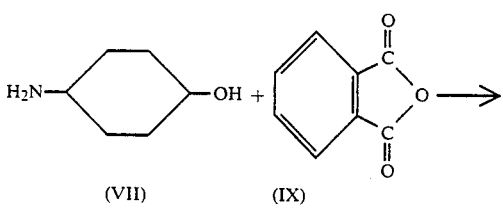
(VII)    (IX)

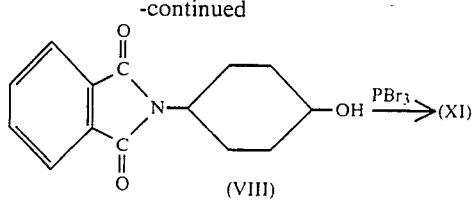
(VIII)

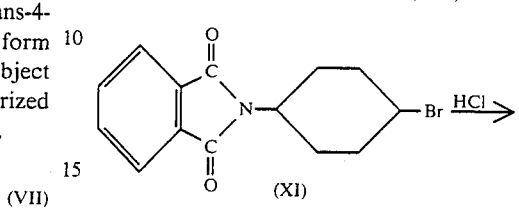
(XI)

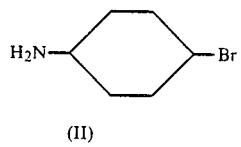
(II)

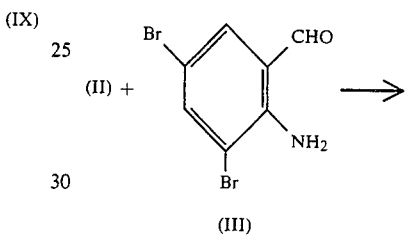
(III)

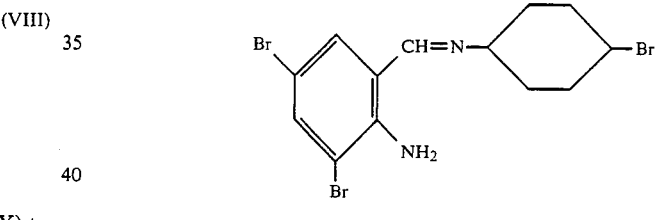
(IV)

$(IV) \xrightarrow{H_2}{Ni/Raney}$

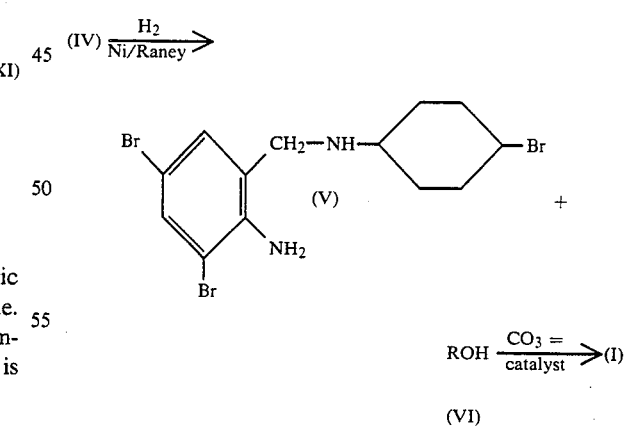
(V)

$ROH \xrightarrow[catalyst]{CO_3=} (I)$ (VI)

The following examples illustrate some forms of the realization of this invention without, however, imposing any limitations of any kind.

EXAMPLE 1

Trans-1-bromocyclohexyl-4-phthalimide (XI)

74 g of phthalic anhydride and 57.6 g of trans-4-aminocyclohexanol are put into a 1-liter flask which is furnished with a stirring means. The mixture is heated in a boiling-water bath for 30 minutes. The initial reation is vigorous. The reaction mixture is cooled to room temperature and the reflux cooler is connected to the flask. 32 ml (91.3 g) of phosphorus tribromide, which has been freshly distilled, are slowly added to the cooled mixture. The reaction mixture is then heated under reflux for 1.25 hours. The hot mixture is then transferred to a vessel containing 750 g of triturated ice. When the ice has completely melted, the raw product, which consists of trans-1-bromocyclohexyl-4-phthalimide, the Büchner filtered and washed with cold water. The raw product is dissolved in 1.2 liters of a 1:1 mixture of water and ethanol with the help of heating. The solution is filtered and cooled in a refrigerator. A white, crystalline product is obtained which has a melting point of 90°–92° C.

EXAMPLE 2

Trans-1-bromo-4-aminocyclohexane hydrochloride (II)

50 g of trans-1-bromocyclohexyl-4-phthalimide are prepared as described in Example 1 and put into a 100 ml flask furnished with recycle-type cooling. 10 ml of water and 60 ml of 12N hydrochloric acid are then added. The solution is heated for 6 hours, under reflux, followed by cooling and filtering of the separated phthalic acid. The solution is evaporated under vacuum and the residue is crystallized with absolute ethylic alcohol. 20 g of trans-1-bromo-4-aminocyclohexane hydrochloride with a melting point of 105°–108° C. are obtained.

EXAMPLE 3

N-(2-amino-3,5-dibromobenzyl)-trans-4-amino-1-bromo-cyclohexane hydrochloride (V)

179 g of trans-1-bromo-4-aminocyclohexane hydrochloride and 279 g of 2-amino-3,5-dibromobenzaldehyde are put into a suitable flask. The temperature rises to 60° C. and the mixture is then cooled to 35° C., after which 250 ml of ethylic alcohol are added. The solution is transferred to a suitable, steel reactor for high-pressure hydrogenizing. 10 g of Nickel-Raney are added, the reactor vessel is closed and hydrogen gas is introduced at 1000 psi. The vessel is agitated at ambient temperature for 15 minutes. The contents of the vessel are poured out and the catalyst is filtered. The ether is evaporated under vacuum. The residue is dissolved in 300 ml of absolute ethylic alcohol followed by the addition of gaseous HCl. THe desired product crystallizes and is recrystallized using absolute ethylic alcohol. 300 g of product are obtained which has a melting point of 240°–245° C.

EXAMPLE 4

N-(2-amino-3,5-dibromobenzyl)-trans-4-amino-1-(guaiacolglycolyl)-cyclohexane (E/6001) hydrochloride 18 g of guaiacolglycolic acid are dissolved in 300 ml of N,N-dimethylformamide, 47.6 g of N-(2-amino-3,5-dibromobenzyl)-trans-4-amino-1-bromo-cyclohexane hydrochloride, 21 g of sodium carbonate and, as a catalyst, 3 g of potassium iodide are added. The reaction is allowed to take place with constant stirring and at ambient temperature. Chromatographic inspection on thin films is made to check how the reaction progresses. At the end of the reaction, which is after about 3 hours, filtering is carried out and the solution is evaporated under vacuum. The residue is dissolved in about 200 ml of ethyl acetate. The solution is filtered and anhydrified on anhydrous magnesium sulphate. The solvent is evaporated under vacuum. The residue is dissolved in 200 ml of absolute ethanol and is then saturated with gaseous hydrochloric acid. About 50 g of desired product are obtained. Spectrum analysis confirms the structure of the obtained compound.

| Analysis for $C_{22}H_{26}Br_2N_2O_4 \cdot HCl$ | | | | M.W.: 578.7 | |
|---|---|---|---|---|---|
| Element: | C | H | N | Br | Cl |
| Calculated %: | 45.66 | 4.53 | 4.84 | 27.62 | 6.30 |
| Found %: | 45.7 | 4.49 | 4.85 | 27.50 | 6.20 |

EXAMPLE 5

N-(2-amino-3,5-dibromobenzyl)-trans-4-amino-1-(4-methylguaiacolglycolyl)cyclohexane (E/6002) hydrochloride The same procedure is used as in Example 4, utilizing 19.4 g of (4-methylguaiacol)glycolic acid instead of 18 g of guaiacolglycolic acid. About 52 g of desired product are obtained with the spectrum analysis confirming the structure of the obtained compound.

| Analysis for $C_{23}H_{28}Br_2N_2O_4 \cdot HCl$ | | | | M.W.: 604.74 | |
|---|---|---|---|---|---|
| Element: | C | H | N | Br | Cl |
| Calculated %: | 47.66 | 4.66 | 4.63 | 26.43 | 6.03 |
| Found %: | 47.8 | 4.68 | 4.65 | 26.5 | 6.02 |

EXAMPLE 6

N-(2-amino-3,5-dibromobenzyl)-trans-4-amino-1-(m-cresolglycolyl)cyclohexane (E/6003) hydrochloride The same procedure is used as in Example 4, using 15 g of m-cresolglycolic acid isntead of 18 g of guaiacolglycolic acid. About 40 g of desired product are obtained with the spectrum analysis confirming the structure of the obtained compound.

| Analysis for $C_{22}H_{26}Br_2N_2O_3 \cdot HCl$ | | | | M.W.: 562.7 | |
|---|---|---|---|---|---|
| Element: | C | H | N | Br | Cl |
| Calculated %: | 46.96 | 4.66 | 4.98 | 28.40 | 6.48 |
| Found %: | 46.85 | 4.7 | 4.25 | 28.35 | 6.45 |

EXAMPLE 7

N-(amino-3,5-dibromobenzyl)-trans-4-amino-1-(o-cresolglycolyl)-cyclohexane (E/6004) hydrochloride The same procedure is used as in Example 4, using 15 g of o-cresolglycolic acid.

48.5 g of desired product are obtained with the spectrum analysis confirming the structure of the obtained compound.

| Analysis for $C_{22}H_{26}Br_2N_2O_3 \cdot HCl$ | | | | M.W.: 562.7 | |
|---|---|---|---|---|---|
| Element: | C | H | N | Br | Cl |
| Calculated % | 46.96 | 4.66 | 4.98 | 28.40 | 6.48 |
| Found %: | 47 | 4.65 | 4.95 | 28.3 | 6.5 |

EXAMPLE 8

N-(2-amino-3,5-dibromobenzyl)-trans-4-amino-1-(p-cresolglycolyl)cyclohexane (E/6005) hydrochloride The same procedure is used as in Example 4, using 15 g of p-cresolglycolic acid instead of 18 g of guaiacolglycolic acid. 48.5 g of desired product are obtained with the spectrum analysis confirming the structure of the obtained compound.

| Analysis for $C_{22}H_{26}Br_2N_2O_3.HCl$ | | | | M.W.: 562.7 | |
|---|---|---|---|---|---|
| Element: | C | H | N | Br | Cl |
| Calculated %: | 46.96 | 4.66 | 4.98 | 28.40 | 6.48 |
| Found %: | 46.98 | 4.7 | 4.95 | 28.35 | 6.38 |

EXAMPLE 9

N-(2-amino-3,5-dibromobenzyl)-trans-4-amino-1-(thymolglycolyl)cyclohexane (E/6006) hydrochloride The same procedure is used as in Example 4, using 17.8 g of thymoglycolic acid instead of 18 g of guaiacolglycolic acid. 51 g of desired product are obtained with the spectrum analysis confirming the structure of the obtained compound.

| Analyis for $C_{24}H_{30}Br_2N_2O_3.HCl$ | | | | M.W.: 590.78 | |
|---|---|---|---|---|---|
| Element: | C | H | N | Br | Cl |
| Calculated %: | 48.79 | 5.12 | 4.74 | 27.05 | 6.17 |
| Found %: | 48.9 | 5.10 | 4.70 | 27 | 6.15 |

EXAMPLE 10

N-(2-amino-3,5-dibromobenzyl)-trans-4-amino-1-(carvacrolglycolyl)cyclohexane (E/6007) hydrochloride The same procedure is used as in Example 4, using 17.8 g of carvacrolglycolic acid instead of 18 g of guaiacolglycolic acid. 51 g of desired product are obtained with the spectrum analysis confirming the structure of the obtained compound.

| Analyis for $C_{24}H_{30}Br_2N_2O_3.HCl$ | | | | M.W.: 590.78 | |
|---|---|---|---|---|---|
| Element: | C | H | N | Br | Cl |
| Calculated %: | 48.79 | 5.12 | 4.74 | 27.05 | 6.17 |
| Found %: | 48.9 | 5.10 | 4.70 | 27 | 6.15 |

Although this invention has been described in detail with reference being made to specific forms of its realization, it is evident that any technician working in this field could make various changes and modifications without exceeding the limits imposed by this invention.

I claim:

1. A compound having formula (I),

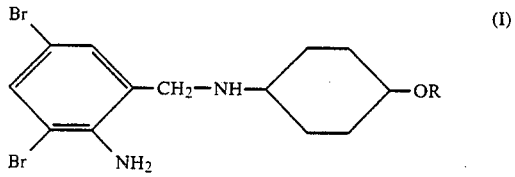

where R represents the groups: guaiacolglycolyl, (4-methylguaiacol)glycolyl, m-cresolglycolyl, o-cresolglycolyl, p-cresolglycolyl, thymolglycolyl, carvacrolglycolyl and guaiacolcarbonyl and pharmaceutically acceptable salts of the same compound.

2. A compound, as per claim 1, wherein it is N-(2-amino-3,5-dibromobenzyl)-trans-4-amino-1-(guaiacolglycolyl)cyclohexane or one of its pharmaceutically acceptable salts.

3. A compound, as per claim 1, wherein it is N-(2-amino-3,5-dibromobenzyl)-trans-4-amino-1-(4-methyl-guaiacolglycolyl)cyclohexane or one of its pharmaceutically acceptable salts.

4. A compound, as per claim 1, wherein it is N-(2-amino-3,5-dibromobenzyl)-trans-4-amino-1-(m-cresolglycolyl)cyclohexane or one of its pharmaceutically acceptable salts.

5. A compound, as per claim 1, wherein it N-(2-amino-3,5-dibromobenzyl)-trans-4-amino-1-(o-cresolglycolyl)cyclohexane or one of its pharmaceutically acceptable salts.

6. A compound, as per claim 1, wherein it N-(2-amino-3,5-dibromobenzyl)-trans-4-amino-1-(p-cresolglycolyl)cyclohexane or one of its pharmaceutically acceptable salts.

7. A compound, as per claim 1, wherein it is N-(2-amino-3,5-dibromobenzyl)-trans-4-amino-1-(thymoglycolyl)cyclohexane or one of its pharmaceutically acceptable salts.

8. A compound, as per claim 1, wherein it is N-(2-amino-3,5-dibromobenzyl)-trans-4-amino-1-(carvacrolglycolyl)cyclohexane or one of its pharmaceutically acceptable salts.

9. A compound, as per one of the preceding claims from 1 to 8, wherein the said pharmaceutically acceptable salt is a salt with the acids; hydrochloric, hydrobromic, hydroiodic, phosphoric, sulphuric, maleic, citric, acetic, oxalic, succinic, benzoic, tartaric, fumaric, mandelic, ascorbic and malic.

10. A compound, as per one of the preceding claims from 2 to 8, wherein the said pharmaceutically acceptable salts is a hydrochloride.

11. A process for the preparation of a compound, as defined in claim 1, wherein trans-1-bromo-4-aminocyclohexane, having formula (II),

is made to react with 2-amino-3,5-dibromobenzaldehyde, having formula (III),

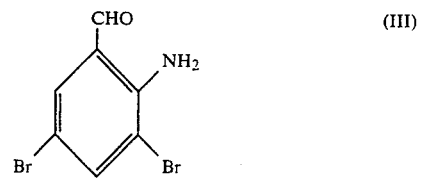

to obtain the aldiminic intermediate having formula (IV),

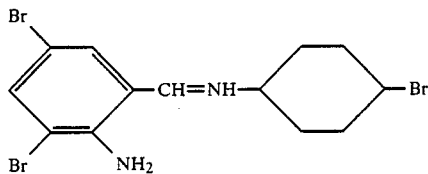

(IV)

which is reduced with hydrogen in the presence of Nickel-Raney to obtain N-(2-amino-3,5-dibromobenzyl)-trans-4-amino-1-bromo-cyclohexane, having formula (V)

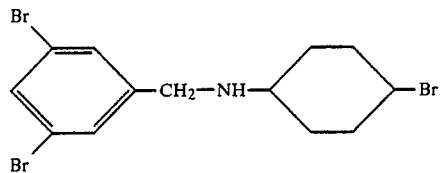

(V)

which is made to react with carboxylic acid having formula (VI),

ROH          (VI)

where R is as defined in claim 1, in the presence of an alkaline carbonate and a catalyst, to obtain the corresponding formula (I) compound, as defined in claim 1, which, optionally, is salified.

12. A process, of claim 11, wherein the reaction between compounds (V) and (VI) is effected in N,N-dimethylformamide.

13. A process, as per one of the preceding claims 11 and 12, wherein the said alkaline carbonate is either sodium or potassium carbonate.

14. A process, as per one of the preceding claims 11 to 13, wherein the said catalyst is either sodium or potassium iodide.

15. A process, as per one of the preceding claims 11 to 14, wherein the formula (II) compound, as defined in claim 11, is obtained in the form of hydrochloride by reacting trans-4-aminocyclohexanol, which has formula (VII)

(VII)

with phthalic anhydride and then with phosphorus tribromide to obtain trans-1-bromocyclohexyl-4-phthalimide, having formula (XI),

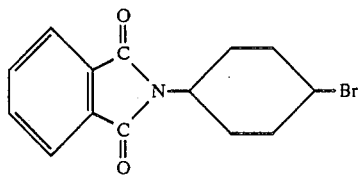

(XI)

which is hydrolyzed with hydrochloric acid to obtain the formula (II) compound.

16. A pharmaceutical composition, wherein it contains, as active principle, an effective quantity of one or more of the compounds as per claim 1, just as they are or in combination with vehicles, diluents, solvents and/or pharmaceutically acceptable excipients.

17. A composition, of claim 16, wherein it is a capsule or pill, which releases the active principle at a normal or a progressively retarded rate, a syrup or emulsion, which is either ready-to-use or extemporaneous, containing from 45 to 135 mg of active principle per posological unit.

18. A composition, of claim 16, wherein it is a vial, which is ready-to-use or extemporaneous, for administration by injection, containing from 15 to 45 mg of active principle.

19. A composition, of claim 16, wherein it is suitable for administration by spraying.

20. A composition, of claim 19, wherein it contains from 15 to 30 mg of active principle per posological unit.

21. A composition, of claim 16, wherein it is suitable for rectal administration and contains from 15 to 90 mg of active principle per posological unit.

* * * * *